US011583188B2

(12) United States Patent
Mitra et al.

(10) Patent No.: US 11,583,188 B2
(45) Date of Patent: Feb. 21, 2023

(54) AUTOMATED DETECTION AND LOCALIZATION OF BLEEDING

(71) Applicant: General Electric Company, Schenectady, NY (US)

(72) Inventors: Jhimli Mitra, Niskayuna, NY (US); Luca Marinelli, Schenectady, NY (US); Asha Singanamalli, Glenville, NY (US)

(73) Assignee: General Electric Company, Schenectady, NY (US)

( * ) Notice: Subject to any disclaimer, the term of this patent is extended or adjusted under 35 U.S.C. 154(b) by 1010 days.

(21) Appl. No.: 16/357,023

(22) Filed: Mar. 18, 2019

(65) Prior Publication Data

US 2020/0297219 A1    Sep. 24, 2020

(51) Int. Cl.
| G06K 9/00 | (2022.01) |
| A61B 5/02 | (2006.01) |
| G06N 3/088 | (2023.01) |
| A61B 8/08 | (2006.01) |
| A61B 5/00 | (2006.01) |
| G06N 20/00 | (2019.01) |

(52) U.S. Cl.
CPC ........ *A61B 5/02042* (2013.01); *A61B 5/7282* (2013.01); *A61B 8/488* (2013.01); *G06N 3/088* (2013.01); *G06N 20/00* (2019.01)

(58) Field of Classification Search
CPC ........ G16H 50/20; G16H 40/67; G16H 15/00; G16H 20/30; G16H 50/30; G16H 20/13; G16H 30/40; G16H 80/00; G16H 40/63; G16H 50/70; G16H 30/20; G16H 10/60; G16H 20/40; G16H 40/20; A61B 5/7264; A61B 5/0077; A61B 5/0022; A61B 5/01; A61B 5/6826; G06T 7/0012; G06T 2207/20084; G06T 2207/30101; G06T 2207/20081; G06T 2207/10056; G06T 2207/30004

See application file for complete search history.

(56) References Cited

U.S. PATENT DOCUMENTS

| 6,083,159 | A | 7/2000 | Driscoll, Jr. et al. |
| 6,955,648 | B2 | 10/2005 | Mozayeni et al. |
| 7,803,116 | B2 | 9/2010 | Sikdar et al. |
| 7,920,731 | B2 | 4/2011 | Moreau-Gobard |
| 8,353,834 | B2 | 1/2013 | Routh et al. |
| 2010/0160781 | A1* | 6/2010 | Carter ............... A61B 8/06 600/439 |
| 2017/0332919 | A1 | 11/2017 | Eagle et al. |

OTHER PUBLICATIONS

Liu, Learning to Diagnose Cirrhosis with Liver Capsule Guided Ultrasound Image Classification, Jan. 2017, MDPI (Year: 2017).*

(Continued)

*Primary Examiner* — Alex Kok S Liew

(57) ABSTRACT

In accordance with the present disclosure, deep-learning techniques are employed to find anomalies corresponding to bleed events. By way of example, a deep convolutional neural network or combination of such networks may be trained to determine the location of a bleed event, such as an internal bleed event, based on ultrasound data acquired at one or more locations on a patient anatomy. Such a technique may be useful in non-clinical settings.

20 Claims, 4 Drawing Sheets

(56) References Cited

OTHER PUBLICATIONS

Jia, Gastrointestinal Bleeding Detection in Wireless Capsule Endoscopy Images Using Handcrafted and CNN Features, 2017, IEEE (Year: 2017).*
Luo, Wenbo, et al.; "Color and Pulsed Doppler Sonography for Arterial Bleeding Detection", J. Ultrasound Med 2007; pp. 1019-1029.
Anand, Ajay, et al.; "Noninvasive Bleeding Detection and Localization Using Three Dimensional Doppler Ultrasound", 2007 IEEE Ultrasonics Symposium Proceedings, 2007, pp. 1297-1300.
Ito, Keiichiro, et al.; "Noninvasive Internal Bleeding Detection Method by Measuring Blood Flow Under Ultrasound Cross-Section Image", 34th Annual International Conference of the IEEE, Engineering in Medicine and Biology Society, 2012, pp. 3191-3194.
Sekins, K. Michael, et al.; "Deep Bleeder Acoustic Coagulation (DBAC)—Part 1: Development and in Vitro Testing of a Research Prototype Cuff System", Journal of Therapeutic Ultrasound, 2015, 27 pages.
Sekins, K. Michael, et al.; "Deep Bleeder Acoustic Coagulation (DBAC)—Part 2: In Vitro Testing of a Research Prototype System", Journal of Therapeutic Ultrasound, 2015, 19 pages.
Jamplis, Robert P., et al; "Point of Care Ultrasound Diagnosis of Upper Gastrointestinal Bleeding", Cureus 9 (12): e1956; DOI 10.7759/cureus. Dec. 17, 2017.

* cited by examiner

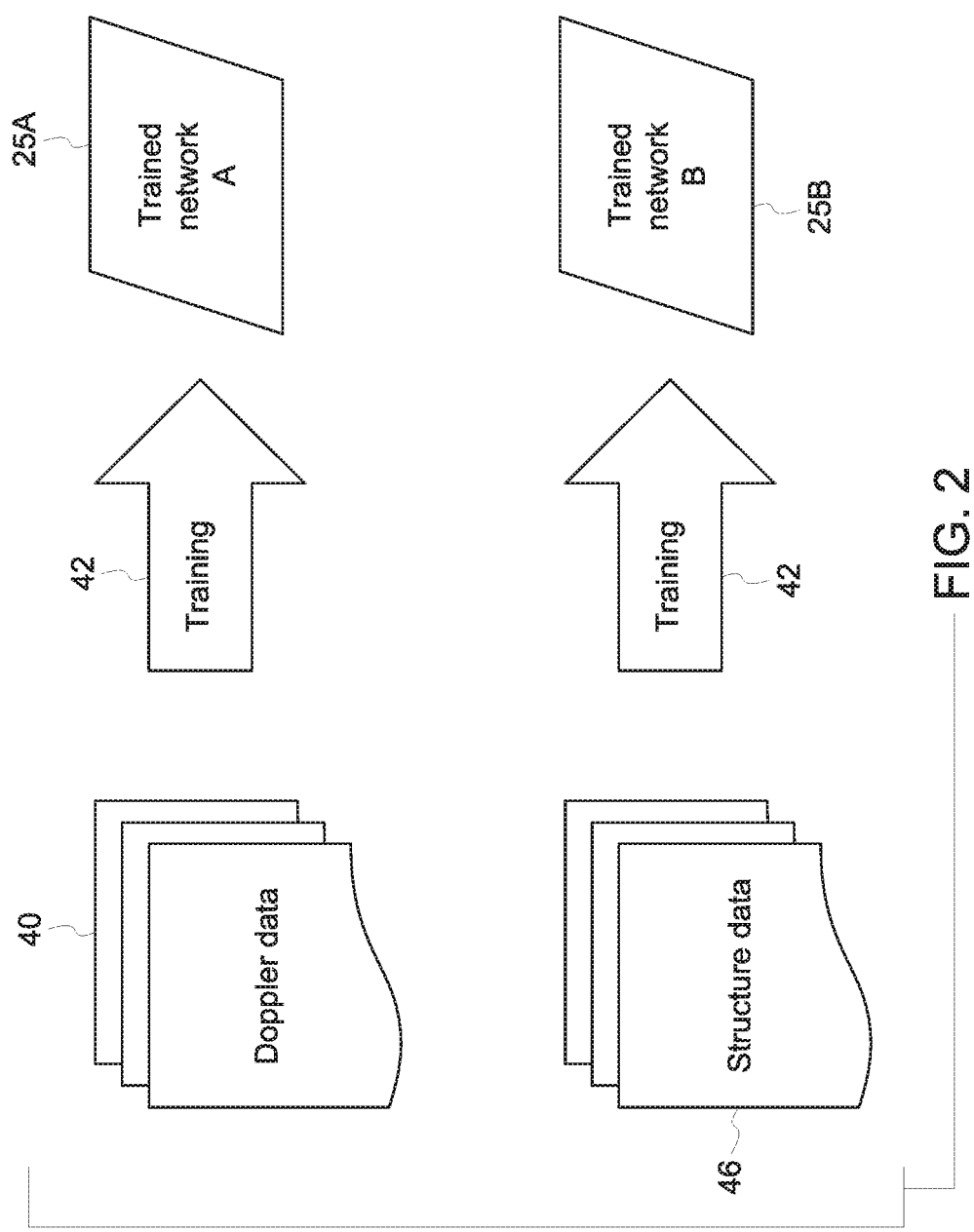

AUTOMATED DETECTION AND LOCALIZATION OF BLEEDING

TECHNICAL FIELD

The subject matter disclosed herein relates to localizing bleeding, including localizing such occurrences outside of a hospital environment.

BACKGROUND

Vascular trauma with vessel disruption can occur in a variety of environments, including both military and civilian environments. In some instances, the vascular trauma may be internal, without a clear break (e.g., an entry or exit wound) in the skin corresponding to the location of the trauma. In such circumstances, it may be difficult to localize where in the body an internal bleeding event is occurring so that treatment can be applied or, indeed, if there is internal bleeding occurring at all. Even in the presence of entry and exit wounds, it may be difficult to ascertain which blood vessel was affected and the location of the bleed.

For example, a skilled or trained person may be able to determine if a bleed event is present based on indications of vascular injury that include pulsatile hemorrhage, expanding hematoma, bruit or thrill over the injury site, absent extremity pulses, and arterial pressure index <0.9. However, such indications may be insufficient to make such a determination even by a trained individual, and likely would be impossible or impractical for an untrained individual to evaluate. Further, even to the extent these factors may allow a skilled or trained person to determine if a vascular injury is present, they may be still insufficient to localize the internal site of the vascular trauma, which is necessary to apply treatment, such as cauterization, that may save a patient from excessive blood loss or death.

BRIEF DESCRIPTION

Certain embodiments commensurate in scope with the originally claimed subject matter are summarized below. These embodiments are not intended to limit the scope of the claimed subject matter, but rather these embodiments are intended only to provide a brief summary of possible embodiments. Indeed, the invention may encompass a variety of forms that may be similar to or different from the embodiments set forth below.

In one embodiment, a method if provided for training one or more neural networks for localization of bleed events. In accordance with this method, a plurality of data representations are acquired. Each data representation corresponds to a healthy region of vasculature. At least one neural network is trained using only the plurality of data representations to generate one or more trained neural networks. The one or more trained neural networks are trained to generate, in response to an input data representation, a synthetic representation based on healthy vasculature, and to output one or more differences between the synthetic representation and the input data representation.

In a further embodiment, a method is provided for localizing a bleed event. In accordance with this method, an input data representation is received as an input to a trained neural network. The input data representation is processed using the trained neural network. Processing the input data representation comprises generating a synthetic representation based on healthy vasculature in response to the input data representation. One or more differences between the synthetic representation and the input data representation are identified. The location of the bleed event is determined using the one or more differences.

In an additional embodiment, a system for localizing bleed events is provided. In accordance with this embodiment, the system comprises: an ultrasound scanner configured to generate ultrasound data at one or more locations of a body of a patient; a memory component configured to store one or more processor-executable routines; and a processing component configured to receive or access the ultrasound data and to execute the one or more processor-executable routines. The one or more routines, when executed by the processing component, cause the processing component to perform acts comprising: receiving respective input data representations as inputs to one or more trained neural networks; processing the respective input data representations using the one or more trained neural networks, wherein processing the respective input data representations comprises generating, on each trained neural network, a respective synthetic representation based on healthy vasculature in response to the respective input data representation; identifying one or more differences between each respective synthetic representation and the respective input data representation; and determining the location of a bleed event using the one or more differences.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein:

FIG. 2 illustrates steps in training neural networks for bleed localization, in accordance with aspects of the present disclosure;

DETAILED DESCRIPTION

Figure 1A:
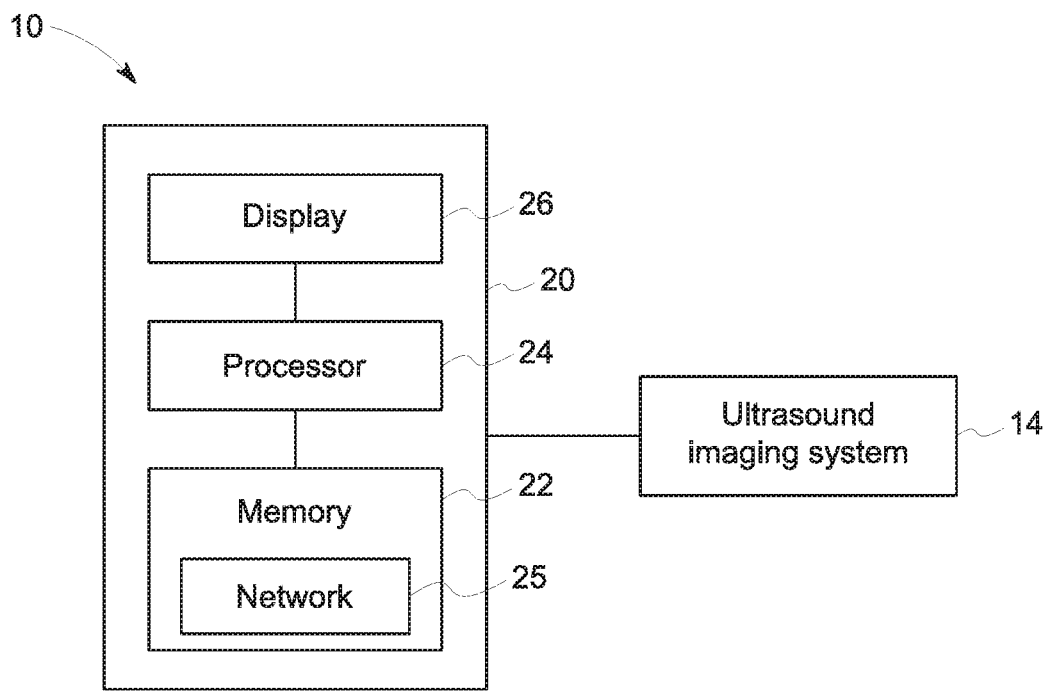
FIGS. 1A and 1B illustrate schematic diagrams of embodiments of an ultrasound-based bleed localization system with (FIG. 1A) and without (FIG. 1B) an associated treatment system, in accordance with aspects of the present disclosure.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

The present disclosure relates to the automatic detection of vascular defects (which in the present context may be equated to a bleeding event) using neural networks in the absence of ground truth knowledge of what is "normal" and "anomalous". In many applications, the notion of normal is known, however, it may be difficult to have previous knowledge of the range of anomalies. In particular, such techniques may not function well when the characteristics or conditions describing the anomalous state are themselves hard to define or highly variable. For example, the problem becomes harder when the range of defects vary in size, geometry or shape, location, and so forth and in many contexts the availability of ground truth 'anomalous' labels is rare.

By way of example, in a medical context, bleed events (what may be considered anomalous in the context of the present disclosure) may vary widely in terms of location, scale, geometry of the wound, and so forth. Additionally, patients vary in terms of their physiology and anatomy and hemodynamic parameters (such as blood pressure). As a result it may be challenging to obtain ground truth labels that may be used to train a machine learning algorithm what an anomalous result (i.e., a bleed event) would look like. In such cases, the traditional supervised machine learning or deep learning approaches may not be applicable where ground-truth labels of both normal and defects are required to train a model or network.

Instead, unsupervised anomaly detection techniques may be employed in which a network is trained using a set of normal instances, but no non-normal or anomalous instances. When an anomalous instance is presented and queried to a neural network trained in this manner, the neural network tries to reconstruct an instance based on normal instances with which the neural network is familiar. The resultant difference between the reconstructed instance and the queried instance presents the anomalies (such as in the form of differences between the queried and reconstructed scenarios. Such an approach may be applied in two or more dimensions (e.g., two-dimensions (2D images), three-dimensions (3D) (e.g., volumetric reconstructions or 2D images over time), of four-dimensions (4D) (e.g., volumes over time).

With this in mind, and in accordance with the present disclosure, deep-learning techniques are employed to find anomalies corresponding to bleed events given that the ground truth label of 'normal' is known. By way of example, a deep convolutional neural network or combination of such networks may be trained to determine the location of a bleed event, such as an internal bleed event, based on ultrasound data acquired at one or more locations on a patient anatomy. Such a technique may be useful in non-clinical settings such as at accident sites, in combat zones, and so forth where both medical equipment and/or trained personnel may be absent.

Based on the derived bleed location, feedback (e.g., location or proximity data) can be provided to a treatment device (such as an automatic cauterization device) or person seeking to evaluate the patient (including conceivably the patient themselves). More generally, once the bleed has been detected and accurately localized, a treatment plan can be formulated and therapy to contain blood loss can be delivered. Conventional therapeutic approaches at the point of care may include application of pressure, hemostatic pads, or the manual or automated application of cauterization, but additional therapies are being explored. For example, balloon catheters for bleeds in major arteries have recently been developed. Detailed information about the location of the bleed as may be acquired using the present techniques would enable deployment of such catheters in a location to maximize therapeutic effectiveness and to minimize side effects. Similarly, high-intensity focused ultrasound (HIFU) may be employed to cauterize a bleed site, with automatic steering of the HIFU beam being accomplished using the bleed location as determined by the techniques discussed herein.

With the preceding in mind, the present techniques may prove beneficial in contexts where trained medical personnel are not readily available, such as in a military context, at an accident site, or in other situations where a person needing evaluation and/or care is not in a clinical environment. Further, bleed localization data obtained using a machine learning and/or deep learning techniques as described herein may be provided to and used by a person or by an automated treatment device (e.g., a cauterization device) capable of treating the bleed using the localization information. In this manner, an individual who is bleeding, including scenarios where the bleeding is internal, may be treated outside a clinical environment so as to reduce or stop the bleeding.

Deep-learning approaches discussed herein may be based on artificial neural networks, and may therefore encompass deep neural networks, fully connected networks, convolutional neural networks (CNNs), auto encoders, decoders, generators and discriminators, recurrent networks, filter banks for convolution, or other neural network architectures. These techniques are referred to herein as deep-learning techniques, though this terminology may also be used specifically in reference to the use of deep neural networks, which is a neural network having a plurality of layers.

As discussed herein, deep-learning techniques (which may also be known as deep machine learning, hierarchical learning, or deep structured learning) are a branch of machine learning techniques that employ mathematical representations of data and artificial neural networks for learning and processing such representations. By way of example, deep-learning approaches may be characterized by their stacking of simple mathematical representations of the data to extract or model high level abstractions of a type of data-of-interest. This may be accomplished using one or more processing layers, with each layer typically corresponding to a different level of abstraction and, therefore potentially employing or utilizing different aspects of the initial data or outputs of a preceding layer (i.e., a hierarchy or cascade of layers) as the target of the processes or algorithms of a given layer. In an image processing or reconstruction context, this may be characterized as different layers corresponding to the different feature levels or resolution in the data. In general, the processing from one representation space to the next-level representation space can be considered as one 'stage' of the process. Each stage of the process can be performed by separate neural networks or by different parts of one larger neural network.

Figure 1B:
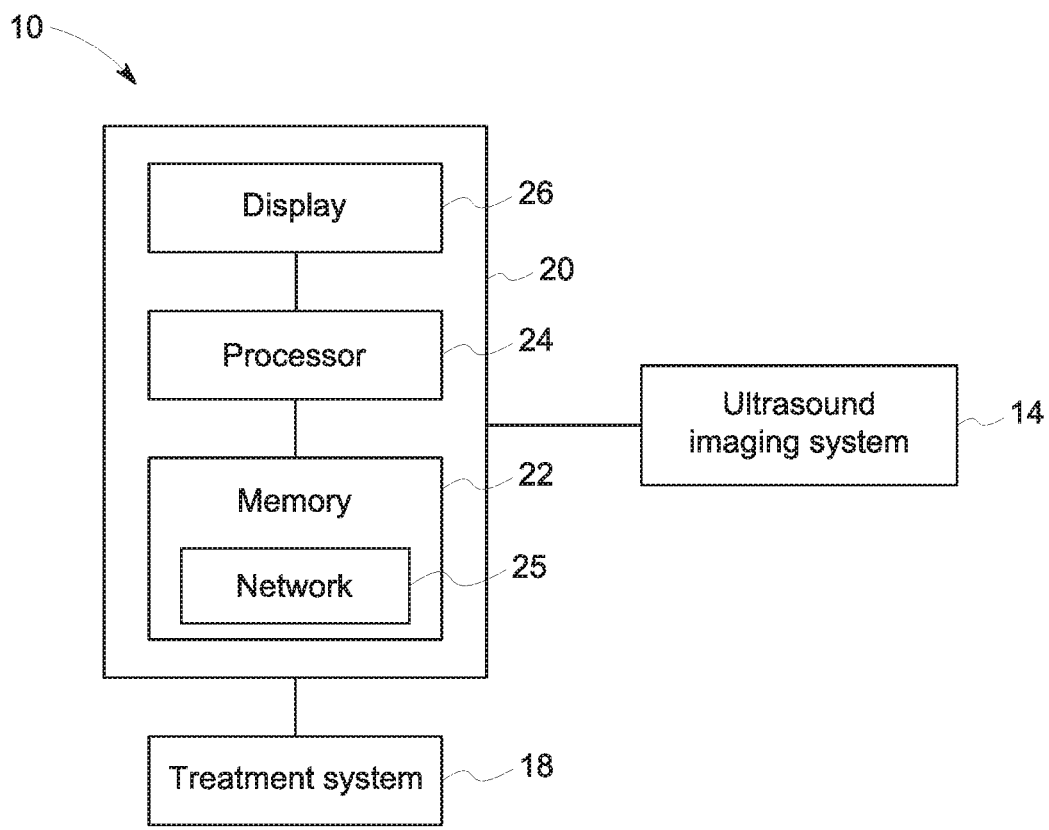

With the preceding comments in mind, FIG. 1A and FIG. 1B illustrate a schematic diagram of an embodiment of a bleed localization system 10 that may be used to identify and localize bleeding, as described herein. The bleed localization system 10 includes or otherwise communicates with an ultrasound imaging system 14, such as a handheld ultrasound imaging system suitable for use in a non-clinical setting (i.e., in the field). The data from the ultrasound system 14 may be stored in a memory 22, which may also contain algorithms or code implementing one or more neural networks 25 or other machine learning algorithms in accordance with the present technique, and may be connected to other data storage or processing systems.

If used in a treatment procedure, the bleed localization system 10 may be in communication with a treatment system 18 (e.g., an automated cauterization system), as shown in FIG. 1B. The treatment system 18 represents an interventional component that utilizes bleed localization information generated by the system 10 to apply an energy-based (e.g., heat or electricity based cauterization) or chemical treatment to a bleed location to reduce or stop the flow of blood.

The bleed localization system 10 may further include a system controller block 20 communicatively coupled to other elements of the bleed localization system 10, such as the ultrasound imaging system 14 and the treatment system 18. The controller 20 may include a memory 22 and a processor 24. In some embodiments, the memory 22 may include one or more tangible, non-transitory, computer-readable media that store instructions executable by the processor 24 and/or data to be processed by the processor 24. For example, the memory 22 may include random access memory (RAM), read only memory (ROM), rewritable non-volatile memory such as flash memory, hard drives, optical discs, and/or the like. Additionally, the processor 24 may include one or more general purpose microprocessors, one or more application specific processors (ASICs), one or more field programmable logic arrays (FPGAs), or any combination thereof. Further, the memory 22 may store instructions executable by the processor 24 to perform the methods described herein. Additionally, the memory 22 may store scan data obtained via the ultrasound imaging system 14 and/or algorithms utilized by the processor 24 to help guide and/or activate the treatment system 18 based on bleed localization information generated based on data acquired using the ultrasound imaging system 14, as discussed in greater detail below. The memory 22 may also store a neural network 25 that when trained functions as an unsupervised deep learning-based bleed localization network as discussed herein. In certain embodiments, the system 10 may be coupled to a remote database that includes the network 25. Further, the controller 20 may include a display 26 that may be used to images and or bleed localization information.

With the preceding mind, in one implementation, the neural networks 25 are trained using unsupervised learning techniques. Such unsupervised learning approaches are useful where a ground truth label of 'normal' is known or can be defined, but where what constitutes an abnormal event may be poorly defined, difficult to comprehensively characterize, or is otherwise unavailable. In the present context, examples of healthy or normal vasculature may be known and may be available for training as to what how healthy vasculature present in the data. Data not conforming to such a healthy or normal presentation may then be characterized as anomalous or abnormal, which in the context of vasculature may correspond to a bleeding event.

In some embodiments, an anomaly detection neural network 25 may be trained using a generative adversarial network (GAN). In general, a GAN utilizes a generator network and a discriminator network as part of an unsupervised machine learning algorithm. The generator network may produce a generated image (e.g., a synthetic image) to estimate a true image and the discriminator network may receive the generated image and the true image (e.g., an input image) and attempt to determine which, of the generated image and the true image, is, in fact, the true image. In learning how to generate accurate image representations and determine the difference between true images and generated images, the generator network and the discriminator network may be balanced such that each learns at a similar rate as the other. In other words, the generator network may attempt to fool the discriminator network by trying to reconstruct the sampled data into an image that appears real, and the discriminator network may learn, over subsequent iterations, how to better determine which image is real and which is generated by the generator network. As discussed herein, learning may refer to updating the code of a neural network, implemented, for example, on a computer. The generator network may be updated after each iteration by the discriminator with an adversarial loss. With each update, the adversarial loss may be used by the generator network to learn how to better fool the discriminator network.

With the preceding in mind, and with reference to FIG. 2, in one embodiment a first anomaly detection network 25A is trained (step 42) using a set of Doppler ultrasound images 40 (or the corresponding unreconstructed Doppler ultrasound data) acquired of normal vasculature (e.g., arteries) that are not experiencing bleed events. In one implementation, the training step 42 comprises using a GAN to train a neural network for use as the anomaly detection network 25A. In this example, the Doppler data 40 typically conveys or represents blood flow in terms of direction and/or velocity, such that the anomaly detection network 25A is trained as to what normal blood flow looks like in a given vascular region.

As discussed herein, in some embodiments more than one neural network 25 may be trained and used for anomaly detection. With this in mind, FIG. 2 also depicts that a second anomaly detection network 25B is trained (step 42) using structural images 46 of the vasculature (or the corresponding unreconstructed structure image data). In such examples, the structure data may be derived from an ultrasound scan or other modalities, such as CT. As in the preceding example, the training step 42 may comprise using a GAN to train a neural network as the anomaly detection network 25B. In this context the structure data 46 typically conveys or represents a normal or healthy vascular structure such that the trained anomaly detection network 25B is trained as to what normal vasculature looks like in a given vascular region. Unlike healthy or normal vascular structures, in the event of a bleed, an artery may be deflated and lose elasticity, exhibiting some structural changes compared to a distended artery with normal blood flow.

Figure 3:
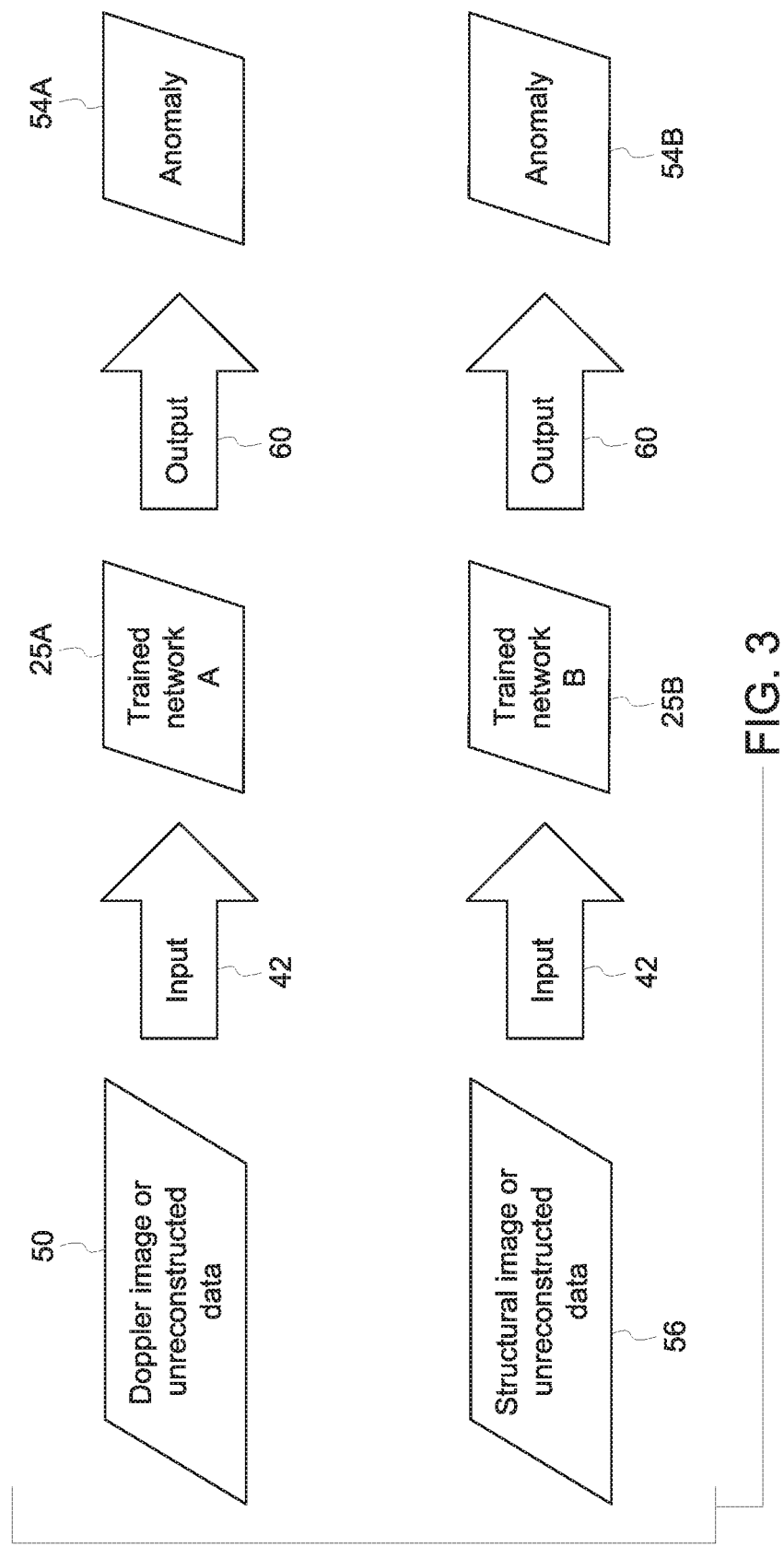
FIG. 3 illustrates steps in using trained neural networks for bleed localization, in accordance with aspects of the present disclosure.

When an image or image data acquired of an anomaly (e.g., an unhealthy or bleeding vessel) is provided as a query or input 42 to the trained neural network(s) 25, the trained network(s) 25 will try to reconstruct the query image based on its training, such as by generating an image in the context of a GAN. In such an implementation, the difference between the input image and the generated image may be used to define or identify the potential anomalies 54 (e.g., a bleed event in the context of vasculature) in the input image. This is represented in FIG. 3 in the context of the trained Doppler-based and structure-based anomaly detection networks 25A, 25B as described above.

In the context of the Doppler-based analysis, an ultrasound scanner (such as a handheld or portable scanner) may be used to acquire Doppler-type ultrasound data 50 that may be provided as an input 42 to the trained Doppler-based anomaly detection network 25A. As discussed herein, the ultrasound data 50 may be reconstructed into a color Doppler image or may be provided in an unreconstructed form. The anomaly detection network 25A attempts to reconstruct the input Doppler image or image data 50 based on its training in the context of the appearance of normal or healthy vasculature. The anomaly detection network 25A may, as an output 60, provide an indication of the difference(s) between the input image or image data 50 and the image or image data generated by the anomaly detection network 25A. These differences may be used to define or identify the potential anomalies 54A discernible in the input Doppler image or image data 50 where the input image or data deviates from how normal or healthy blood flow direction and/or velocity should appear in the present context.

Similarly, in the context of the structure-based analysis, an ultrasound scanner (such as a handheld or portable scanner) or other suitable structure imaging modality may be used to acquire data 56 that may be provided as an input 42 to the trained structure-based anomaly detection network 25B. As discussed herein, the structure data 56 may be reconstructed into an image representative of vascular structure or may be provided in an unreconstructed form. The anomaly detection network 25B attempts to reconstruct the input structure image or image data 50 based on its training in the context of the appearance of normal or healthy vasculature. The anomaly detection network 25B may, as an output 60, provide an indication of the difference(s) between the input image or image data 50 and the image or image data generated by the anomaly detection network 25B. These differences may be used to define or identify the potential anomalies 54B discernible in the input structure image or image data 50 where the input image or data deviates from how normal or healthy vascular structures should appear in the present context.

Figure 4:
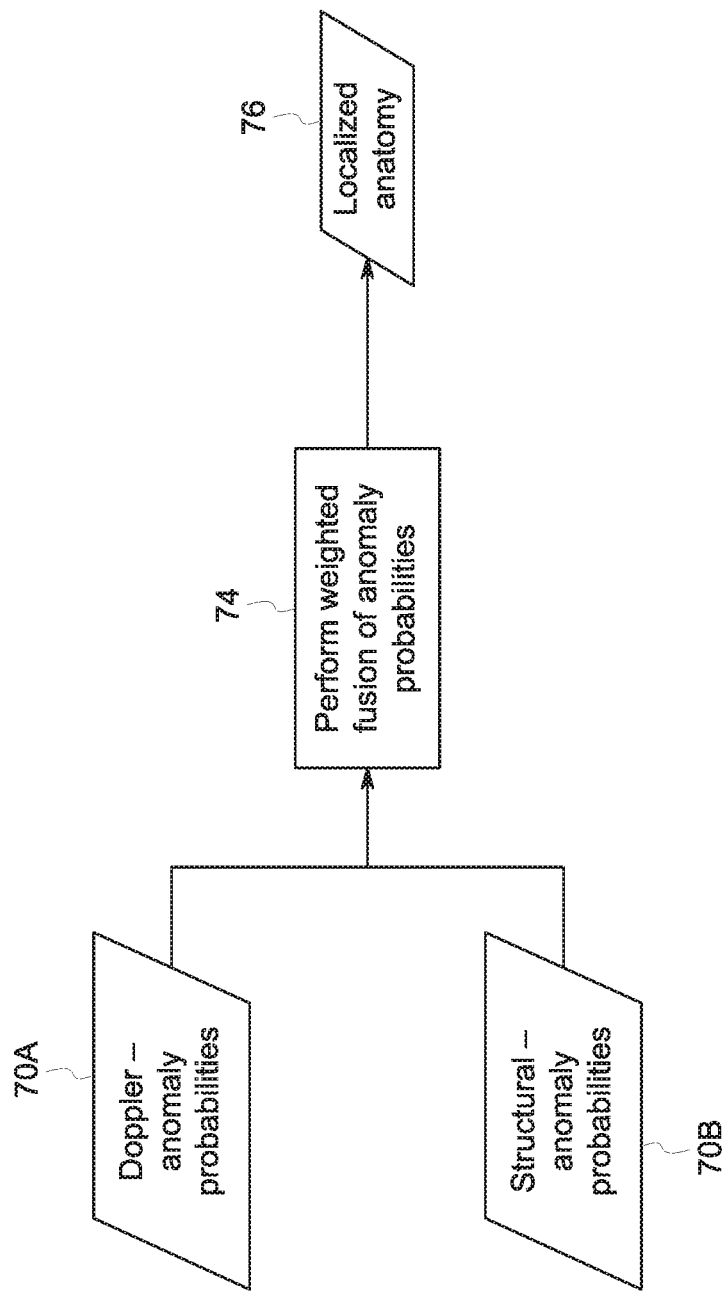
FIG. 4 illustrates steps in fusing different neural network outputs to locate an anatomic region where a bleed event is present, in accordance with aspects of the present disclosure.

As may be ascertained from the above examples, in implementations in which multiple trained neural networks 25 are employed, multiple outputs 60 related to possible anomalies are also obtained. With this in mind, and turning to FIG. 4, the respective outputs 70A, 70B of two neural networks 25 (e.g., a Doppler-based anomaly detection network 25A and a structure-based anomaly detection network 25B) are provided. In this example, the respective outputs may associate different probabilities of a bleed event with different locations or coordinates of a patient. The respective outputs 70A and 70B of the differently trained neural networks 25A, 25B may be combined or aggregated to derive the anatomic location 76 at which a bleed event exists. In one embodiment, the anatomic location 76 may be derived from the multiple outputs by performing a weighted fusion (step 74) where weighting may be applied or performed based on the various factors, such as the anatomic region in question, the modality, quantitative and/or qualitative factors associated with data quality, statistical measures of confidence for the respective separate probabilistic values, empirical or historical data from which weights can be derived and so forth. Thresholds may also be applied at this stage to limit the impact of individual probabilistic assessments when more than one is present or to provide determinative assessments when one measure is determined to be sufficiently dominant or certain.

As noted above, once the anatomic location 76 of the bleed is determined, a treatment plan can be formulated and an appropriate therapy applied to limit and/or stop blood loss. Such therapeutic approaches at the point of care may include, but are not limited to, application of pressure or hemostatic pads, cauterization using HIFU, or deployment of such balloon catheters at the determined location Technical effects of the invention include the use of unsupervised anomaly detection on one or more sets of image data, such as on color Doppler ultrasound and structural ultrasound image data to localize a bleed event. A further technical effect is the combination or fusion of anomaly detection outcomes from different neural networks, such as two different networks trained on color Doppler and structural ultrasound respectively, for accurate localization of bleed events. A real-world effect of the present teachings is the ability to localize (and treat) bleed events in a non-clinical setting and/or by individuals without clinical backgrounds or training, such as in an emergency setting.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for training one or more neural networks for localization of bleed events, the method comprising:
   acquiring a plurality of data representations, wherein each data representation corresponds to a healthy region of vasculature;
   training at least one neural network using only the plurality of data representations to generate one or more trained neural networks, wherein the one or more trained neural networks are trained to generate, in response to an input data representation, a synthetic representation based on healthy vasculature, and to output one or more differences between the synthetic representation and the input data representation.

2. The method of claim 1, wherein each data representation corresponds to a healthy region of vasculature in which no bleeds are present.

3. The method of claim 1, wherein the input data representation and the data representations of the plurality of data representations are images.

4. The method of claim 1, wherein the input data representation and the data representations of the plurality of data representations are unreconstructed image data.

5. The method of claim 1, wherein the input data representation and the data representations of the plurality of data representations are one or more of Doppler ultrasound data, structural ultrasound data, or computed tomography structural data.

6. The method of claim 1, wherein the one or more differences correspond to bleed locations.

7. The method of claim 1, wherein training the at least one neural network comprises training the at least one neural network using a generative adversarial network to implement an unsupervised machine learning process.

8. A method for localizing a bleed event, the method comprising:
   receiving an input data representation as an input to a trained neural network;
   processing the input data representation using the trained neural network, wherein processing the input data representation comprises generating a synthetic representation based on healthy vasculature in response to the input data representation;

identifying one or more differences between the synthetic representation and the input data representation; and determining the location of the bleed event using the one or more differences.

9. The method of claim 8, further comprising:

providing the input data representation or a different input data representation to a different trained neural network;

generating, on the different trained neural network, a different synthetic representation based on healthy vasculature in response to the input data representation or the different input data representation;

identifying one or more additional differences between the different synthetic representation and the input data representation or the different input data representation; and determining the location of a bleed event using the one or more differences and the one or more additional differences.

10. The method of claim 9, wherein the trained neural network is trained to process reconstructed or unreconstructed Doppler ultrasound data and the different trained neural network is trained to process reconstructed or unreconstructed structural ultrasound data.

11. The method of claim 9, wherein determining the location of the bleed event comprises performing a weighted combination of the one or more differences and the one or more additional differences.

12. The method of claim 11, wherein the weighted combination is based on one or more probabilities associated with respective differences.

13. The method of claim 11, wherein the weighted combination is based on one or more threshold operations.

14. The method of claim 8, wherein the trained neural network is trained using unsupervised learning using only data representations of healthy vasculature.

15. The method of claim 8, further comprising:

providing the location of the bleed event to a person to perform a treatment.

16. The method of claim 8, further comprising:

providing the location of the bleed event to a treatment device to automatically perform a treatment.

17. A system for localizing bleed events, comprising:

an ultrasound scanner configured to generate ultrasound data at one or more locations of a body of a patient;

a memory component configured to store one or more processor-executable routines; and a processing component configured to receive or access the ultrasound data and to execute the one or more processor-executable routines, wherein the one or more routines, when executed by the processing component, cause the processing component to perform acts comprising:

receiving respective input data representations as inputs to one or more trained neural networks;

processing the respective input data representations using the one or more trained neural networks, wherein processing the respective input data representations comprises generating, on each trained neural network, a respective synthetic representation based on healthy vasculature in response to the respective input data representation;

identifying one or more differences between each respective synthetic representation and the respective input data representation; and determining the location of a bleed event using the one or more differences.

18. The system of claim 17, wherein one of the one or more trained neural networks is trained to process reconstructed or unreconstructed Doppler ultrasound data and another of the trained neural networks is trained to process reconstructed or unreconstructed structural ultrasound data.

19. The system of claim 17, wherein determining the location of the bleed event comprises performing a weighted combination of the one or more differences from different trained neural networks.

20. The system of claim 17, wherein the one or more trained neural networks are trained using unsupervised learning using only data representations of healthy vasculature.

* * * * *